United States Patent [19]

Kosanetzky et al.

[11] Patent Number: 5,150,395
[45] Date of Patent: Sep. 22, 1992

[54] DEVICE FOR EXAMINING A TEST OBJECT BY MEANS OF GAMMA OR X-RAYS

[75] Inventors: Josef Kosanetzky, Norderstedt; Karl H. Fischer, Hamburg, both of Fed. Rep. of Germany

[73] Assignee: U.S. Philips Corporation, New York, N.Y.

[21] Appl. No.: 638,255

[22] Filed: Jan. 4, 1991

[30] Foreign Application Priority Data

Jan. 10, 1990 [DE] Fed. Rep. of Germany ....... 4000507

[51] Int. Cl.⁵ .............................................. G01N 23/20
[52] U.S. Cl. ...................................... 378/86; 378/87; 378/148; 378/149
[58] Field of Search ................ 378/6, 7, 86–90, 378/146–153, 154, 155

[56] References Cited

U.S. PATENT DOCUMENTS

| | | | |
|---|---|---|---|
| 4,118,632 | 10/1978 | Luig | 378/158 |
| 4,423,422 | 12/1983 | Harding | 378/6 |
| 4,480,332 | 10/1984 | Strecker | 378/6 |
| 4,750,196 | 6/1988 | Harding | 378/87 |
| 4,809,312 | 2/1989 | Annis | 378/87 |
| 4,899,283 | 2/1990 | Annis | 378/146 |
| 4,918,712 | 4/1990 | Le Floc'h et al. | 378/86 |

FOREIGN PATENT DOCUMENTS 8800697 1/1988 PCT Int'l Appl. .

Primary Examiner—David P. Porta
Attorney, Agent, or Firm—William Squire

[57] ABSTRACT

A device for examining a test object (4) by means of gamma or X-rays, comprising a primary X-ray source for generating at least one primary X-ray pencil beam (3) which is directed onto the test object (4), and at least one slit diaphragm (8, 9) which is arranged between the test object (4) and a detector (6, 7) and which directs scattered X-rays (26, 27, 28, 29) produced by the primary X-ray beam (3) in the test object (4) onto at least one detector (6, 7). The depth range of the test object that can be covered by the detectors can be changed without changing the position of the test object or the examination device, in that the position of the slit diaphragm (8, 9) relative to the detector (6, 7) can be changed by means of an adjusting device (18, 19).

22 Claims, 1 Drawing Sheet

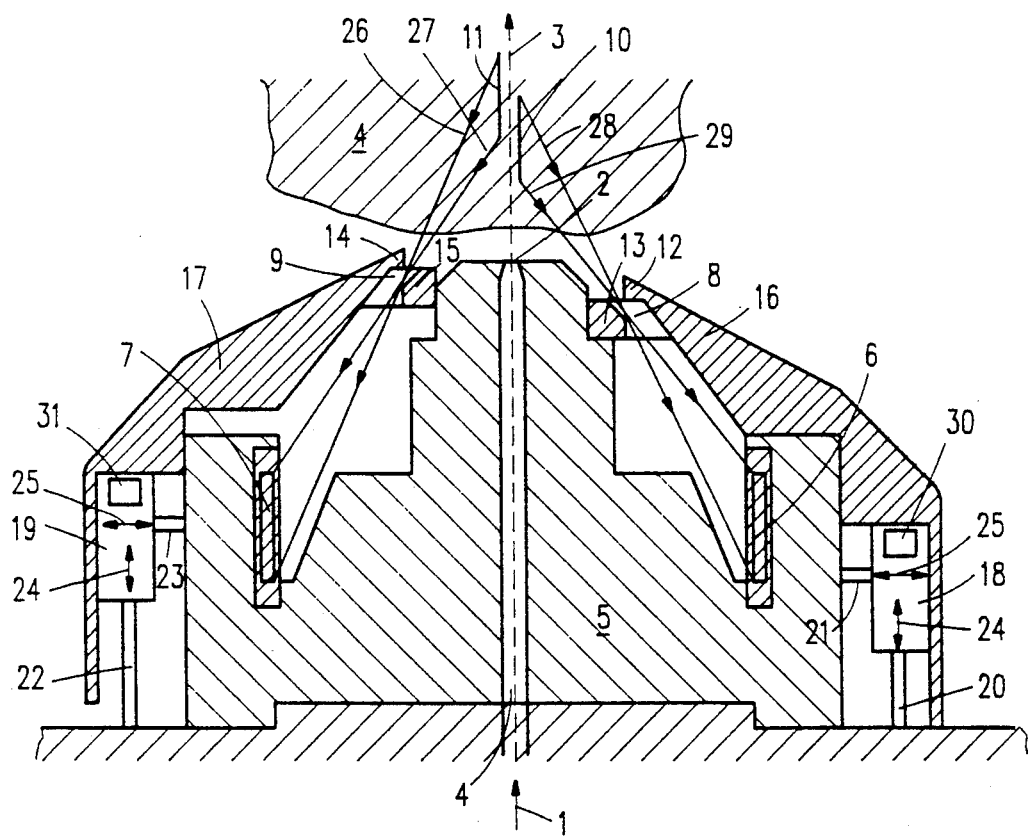

DEVICE FOR EXAMINING A TEST OBJECT BY MEANS OF GAMMA OR X-RAYS

BACKGROUND OF THE INVENTION

The invention relates to a device for examining a test object by means of gamma or X-rays, comprising a primary X-ray source for generating at least one primary X-ray pencil beam which is directed onto the test object, and also comprising at least one slit diaphragm which is arranged between the test object and a detector and which directs secondary X-rays (Compton effect) produced by the primary X-rays in the test object onto at least one detector.

Devices of this kind are known from EP-A 184 247 which corresponds to U.S. Pat. No. 4,750,196 and are used for the non-destructive testing of high-quality components, for example components used in the aerospace industry.

The intensity of the pencil-shaped primary X-ray beam penetrating the material of the test object is changed due to absorption and scattering. As the primary radiation energy is higher, the Compton scattering becomes dominant, which scattering propagates substantially spherically from each point of the material on the path of the primary radiation. The intensity of the Compton scattering, therefore, is substantially equal in all angular directions. Notably materials such as light metal, plastics, laminates or ceramics can notably be advantageously tested.

Particularly simple test devices are obtained when the components of the secondary radiation which are backscattered relative to the primary radiation direction are detected by suitable detectors. The detectors are then arranged on the same side of the test object as the primary X-ray source.

The slit diaphragm operates in the same way as a pinhole camera. Its position in space relative to the detector determines from which of the points of the test object, situated on the primary beam path, scattered radiation reaches the detector. A three-dimensional zone of the test object can be examined by displacement of the test object relative to the examination device or vice versa.

Points of the test object which succeed one another in the direction of the primary X-ray beam in a given depth range can be scanned without displacement of the test object or the examination device if use is made of array of several detectors. Furthermore, the primary X-ray beam can be shifted perpendicularly to the beam direction by means of a suitable deflection device, for example as described in EP-A 184 247, so that surfaces of the test object can be scanned without intricate displacement of the examination device.

For a predetermined spatial relationship between the test object and the examination device, the depth range that can be measured is predetermined by the geometrical relationship between the position of the slit diaphragm and the detectors.

SUMMARY OF THE INVENTION

It is an object of the invention to construct device of the kind set forth so that the depth range of the test object that can be covered by the detectors can be changed without changing the position of the test object or the examination device.

This object is achieved in that the position of the slit diaphragm with respect to the detector can be changed by means of an adjusting device.

In accordance with the invention, only a small component of the examination device which comprises a slit diaphragm or a detector need be adjusted. This can be simply realized with a high degree of precision. It is particularly simple to change the position of the slit diaphragm.

The relative position of the slit diaphragm predetermines the test object depth wherefrom secondary radiation is detected by a detector. When use is made of an array of several detectors, the position of the slit diaphragm can also influence the distance between the points covered by the detectors. Thus, if only the resolution is to be changed by an array of detectors, i.e. the distance between the individual associated measuring points, the slit diaphragm is preferably displaced in a coordinate direction which corresponds to the central axis of the secondary radiation passing through the slit. However, if the individual points are to be shifted together in the direction of the primary beam without changing their spacing, the coordinate direction of the displacement should preferably be inclined with respect to the central axis of the scattered radiation. In that case it is generally sufficient that the coordinate direction extends parallel to the central axis of the secondary X-rays; this can be achieved in a structurally simple manner. According to this simple solution, the spacing between the individual points detected is only insignificantly changed.

If the position in depth as well as the spacing of the points detected is to be varied, the slit diaphragm or the detector should be displaceable in two coordinate directions.

An easy-to-handle examination device is obtained when the slit diaphragm or the detector is displaceable in at least one coordinate direction by means of a manipulator. According to a preferred solution, the manipulator can be driven by means of an electric motor. In that case adjusting operations can be initiated on a control desk in an arbitrary location.

When the electric motors of the manipulator can be controlled via programmable control circuits, measuring points situated in a given area can be automatically scanned. The measuring values for the individual points can be stored so as to form an overall image.

The invention will be described in detail hereinafter with reference to the accompanying drawing.

BRIEF DESCRIPTION OF THE DRAWING

The FIGURE is a sectional view of the measuring head of a device for the non-destructive testing of a test object in accordance with the invention.

DESCRIPTION OF THE PREFERRED EMBODIMENTS

X-rays 1 emanating from an X-ray source (not shown) of an arbitrary known type, penetrate a test object 4 as a pencil beam 3 after emanating from slit 2 via a channel 30 of the measuring head 5. In all points on its path through the test object, scattered radiation is dispersed in all angular directions, the intensity of the radiation being dependent on the kind of matter. The slit diaphragms 8 and 9, which are positioned on axes symmetrical relative to beam 3 but which can assume different relative axial positions parallel to beam 3 permit secondary rays to pass therethrough from predetermined points to detector arrays 6 and 7 which are rigidly arranged in the measuring head 5. Each of these detector arrays consist of, for example five individual detectors which are arranged one over the other in a linear array in the direction of the primary beam 3, so that a detector array 6 or 7 covers five points of a depth zone 10 or a depth zone 11, respectively.

The points covered by the two detector arrays 6 and 7 generally are not identical; for example, they follow one another in an alternating and offset fashion. A single detector array comprising a single detector in principle suffices for a device in accordance with the invention. A plurality of detectors, however, is advantageous in order to reduce the measuring times by the simultaneous execution of parallel measurements. This is because the multitude of measuring points to be scanned and the measuring times required for noise suppression lead to substantial measuring periods for the examination of a test object.

The slit diaphragms 8 and 9 are formed, between slit rims 12, 13 and 14, 15, respectively of diaphragm members 16 and 17, respectively. These diaphragm members are independently adjustable in the direction of the double arrows 24 and 25, respectively, by means of motorized manipulators 18 and 19, respectively, via spindles 20, 21 and 22, 23, respectively.

When the right-hand diaphragm member 16 is in an extreme lower position, the left-hand diaphragm member 17 is lifted to a lifted position. Therefore, the secondary extreme rays 26 and 27 reaching the detector array 7 define a depth zone 11 which is higher than the depth zone 10 between the secondary extreme rays 28 and 29 reaching the detector array 6.

The motorized manipulators 18 and 19 include electric motors (not shown) which are controlled by programmable control circuits 30 and 31, respectively. The control circuits may be programmed so that measuring points are successively covered in different depth zones in an automatic sequence. The measurement data is stored and ultimately displayed on a display screen (not shown).

When a deflection device (see EP-A 184 247) is provided for the primary beam (not shown for the sake of simplicity), a flat surface area of the test object 4 can be imaged. When the measuring head is additionally displaceable over a given range in a third coordinate direction, three-dimensional parts of the test object 4 can be imaged.

A suitable change of the depth range covered by the examination is possible when the slit diaphragm is adjustable only in the directions of the arrow 24 of the primary beam 3. In that case a particularly simple construction of the adjusting mechanism is obtained, in which the diaphragm members 16 and 17 can be displaced together as one structural unit.

What is claimed is:

1. A device for detecting X-ray or gamma radiation scattered by an object in response to an incident radiation pencil beam, said device comprising:
a body;
at least one slit diaphragm secured to a body;
at least one detector secured to the body, said at least one slit diaphragm for directing said scattered radiation onto said at least one detector; and
adjusting means for changing the relative position of the at least one diaphragm to the at least one detector, each diaphragm position corresponding to a different region of the object producing said directed scattered radiation.

2. The device of claim 1 wherein said adjusting means includes means for adjusting the position of said at least one diaphragm.

3. The device of claim 1 wherein said adjusting means includes means for adjusting the position of the at least one diaphragm in a single coordinate direction.

4. The device of claim 3 wherein said scattered radiation has a central axis, said coordinate direction being inclined relative to said central axis.

5. The device of claim 1 wherein said adjusting means includes means for adjusting the position of said at least one diaphragm in two coordinate directions.

6. The device of claim 5 wherein said scattered radiation has a central axis, said coordinate directions being inclined relative to said central axis.

7. The device of claim 1 wherein said adjusting means includes a manipulator secured to said body and to said at least one diaphragm.

8. The device of claim 6 wherein said adjusting means includes a manipulator secured to said body and to said at least one diaphragm.

9. The device of claim 7 wherein said manipulator is motorized.

10. The device of claim 8 wherein said manipulator is motorized.

11. The device of claim 9 including programmable control means for operating said manipulator.

12. The device of claim 10 including programmable control means for operating said manipulator.

13. The device of claim 1 wherein said body has a channel for forming incident radiation into said pencil beam.

14. The device of claim 12 wherein said body has a channel for forming incident radiation into said pencil beam.

15. The device of claim 13 wherein the channel has an exit slit on a side of said body, said at least one slit diaphragm being located on said body side adjacent to said slit.

16. The device of claim 15 including a plurality of said at least one slit diaphragm, said plurality of diaphragms being positioned on axes symmetrical relative to said exit slit.

17. The device of claim 13 wherein said at least one detector comprises a plurality of detectors arranged in an array.

18. The device of claim 17 wherein said channel is linear, said array being linear and parallel to said channel.

19. The head of claim 1 wherein each diaphragm position corresponds to a different depth range in the object.

20. A radiation measuring head for measuring radiation scattered by an object comprising:
a body, said body having a channel with an exit slit for forming incident radiation into a radiation pencil beam;
a diaphragm member adjacent to said exit slit for receiving and directing radiation scattered by said object receiving said pencil beam;
detector means arranged to receive said directed radiation from said diaphragm member; and
means for adjusting the relative position of the diaphragm member to said detector, each position of the diaphragm member corresponding to a different region of the object producing said directed scattered radiation.

21. The head of claim 20 including a pair of said diaphragm members on opposing sides of said exit slit.

22. The head of claim 21 wherein said adjusting means includes means for adjusting the position of said diaphragm members so that the members have different positions relative to said exit slit for receiving scattered radiation from different depth ranges of said object.

* * * * *